(12) United States Patent
Uyama et al.

(10) Patent No.: US 8,859,245 B2
(45) Date of Patent: Oct. 14, 2014

(54) METHOD FOR SEPARATION OF LACTIC ACID COMPONENT FROM LACTIC ACID FERMENTATION LIQUOR, AND SEPARATION APPARATUS

(75) Inventors: Hiroshi Uyama, Osaka (JP); Hideo Noda, Amagasaki (JP); Takahiko Terada, Amagasaki (JP)

(73) Assignees: Bio-Energy Corporation, Hyogo (JP); Osaka University, Osaka (JP); Kansai Chemical Engineering Co., Ltd., Hyogo (JP)

(*) Notice: Subject to any disclaimer, the term of this patent is extended or adjusted under 35 U.S.C. 154(b) by 1313 days.

(21) Appl. No.: 12/294,376

(22) PCT Filed: Mar. 8, 2007

(86) PCT No.: PCT/JP2007/055165
§ 371 (c)(1),
(2), (4) Date: Sep. 24, 2008

(87) PCT Pub. No.: WO2007/114017
PCT Pub. Date: Oct. 11, 2007

(65) Prior Publication Data
US 2009/0093034 A1    Apr. 9, 2009

(30) Foreign Application Priority Data
Mar. 29, 2006   (JP) .................................. 2006-092355

(51) Int. Cl.
*C12P 7/62* (2006.01)
*C12P 7/00* (2006.01)
*B01D 11/04* (2006.01)
*C07C 51/48* (2006.01)

(52) U.S. Cl.
CPC ............ *B01D 11/0488* (2013.01); *C07C 51/48* (2013.01)
USPC ........................................ 435/135; 435/132

(58) Field of Classification Search
USPC ................................................ 435/135, 132
See application file for complete search history.

(56) References Cited

U.S. PATENT DOCUMENTS

| | | | |
|---|---|---|---|
| 5,319,107 A | 6/1994 | Benecke et al. | |
| 5,359,027 A * | 10/1994 | Perego et al. | 528/354 |
| 5,420,304 A | 5/1995 | Verser et al. | |
| 5,686,630 A | 11/1997 | Miso et al. | |
| 6,187,951 B1 * | 2/2001 | Baniel et al. | 562/580 |
| 6,229,046 B1 | 5/2001 | Eyal et al. | |
| 6,489,508 B1 * | 12/2002 | Van Gansbeghe et al. | 562/589 |
| 7,026,145 B2 | 4/2006 | Mizrahi et al. | |
| 2002/0132967 A1 | 9/2002 | Ohara et al. | |

FOREIGN PATENT DOCUMENTS

| | | |
|---|---|---|
| EP | 0614983 A2 | 9/1994 |
| EP | 0657542 A1 | 6/1995 |
| GB | 620320 A | 3/1949 |
| JP | 05260964 A | 10/1993 |
| JP | 6070679 A | 3/1994 |
| JP | 6311886 A | 11/1994 |
| JP | 7155191 A | 6/1995 |
| JP | 10287668 A | 10/1998 |
| JP | 2001519178 A | 10/2001 |
| JP | 2002300898 A | 10/2002 |
| JP | 2003073330 A | 3/2003 |
| JP | 2003159091 A | 6/2003 |
| JP | 2005270025 A | 10/2005 |
| WO | 0125180 A1 | 4/2001 |

OTHER PUBLICATIONS

Kempe et al. Effect of Continuously Controlled pH on Lactic Acid Fermentation. 1950. Industrial and Engineering Chemistry pp. 1852-1857.*
Yamada, et al., "Preparation and Selective Separation of Cyclic Poly-Lactic Acid", The Chemical Society of Japan Koen Yokoshu (2001), vol. 80, p. 299, 3P4A-22, Sep. 7, 2001 (5 pp.), partial English translation (2 pp.).
Proikakis, C.S. et al., "Synthesis and Characterization of Low Molecular Weight Polylactic Acid", Journal of Elastomers and Plastics, vol. 34, Jan. 2002, pp. 49-63 (16 pp.).

* cited by examiner

*Primary Examiner* — Karen Cochrane Carlson
*Assistant Examiner* — Natalie Moss
(74) *Attorney, Agent, or Firm* — The Webb Law Firm

(57) ABSTRACT

A lactic acid component (e.g., lactic acid or oligo (lactic acid)) can be obtained by extraction from a lactic acid fermentation liquor with a pH of 4.8 or less, using at least one solvent selected from the group consisting of toluene, xylene, mesitylene, ethylbenzene, methanol, ethanol, propanol, butanol, and mineral spirit. Furthermore, oligo (lactic acid) can be obtained, by heating a lactic acid fermentation liquor with a pH of 4.8 or less under reduced pressure, and washing, with water, the fermentation liquor containing a produced oligo (lactic acid). Hence, a method is provided for separating a lactic acid component from a lactic acid fermentation liquor, which is free from incorporation of impurities and which includes simple steps.

3 Claims, 1 Drawing Sheet

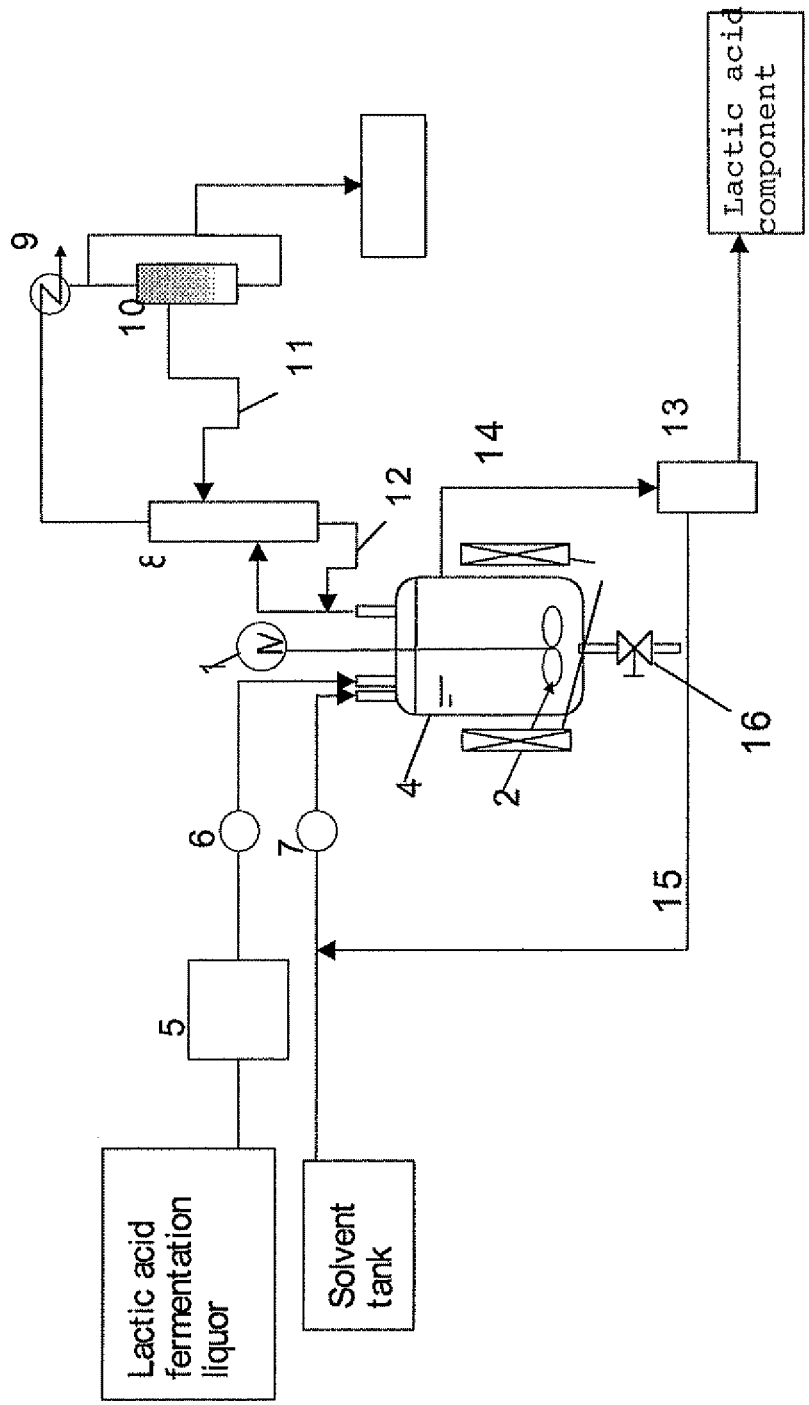

METHOD FOR SEPARATION OF LACTIC ACID COMPONENT FROM LACTIC ACID FERMENTATION LIQUOR, AND SEPARATION APPARATUS

TECHNICAL FIELD

The present invention relates to methods for separating a lactic acid component from a lactic acid fermentation liquor, and apparatuses for the same.

BACKGROUND ART

Conventionally, a lactic acid component is separated from a lactic acid fermentation liquor using, for example, a method for collecting a lactic acid component in the form of a lactic acid ester, a method for collecting a lactic acid component in the form of calcium lactate, or a method for separating a lactic acid component by electrodialysis.

As the method for collecting a lactic acid component in the form of a lactic acid ester, a method is disclosed in which a lactic acid ester is synthesized by adding butanol or pentanol to ammonium lactate generated by fermentation, and collected by distillation (for example, Japanese Laid-Open Patent Publication No. 6-311886).

As the method for collecting a lactic acid component in the form of calcium lactate, a method is disclosed in which lactic acid obtained from fermentation is neutralized with calcium hydroxide or calcium carbonate to generate calcium lactate precipitates for collection (for example, Japanese Laid-Open Patent Publication No. 6-070679).

As the method using electrodialysis, a method is disclosed in which a lactic acid fermentation liquor is introduced into a desalting chamber of an electrodialysis cell with which an anode, a cathode, and alternately arranged cation exchange membranes and anion exchange membranes are provided, and thus salts of lactic acid is concentrated in the fermentation liquor and separated (for example, Japanese Laid-Open Patent Publication No. 7-155191).

Japanese Laid-Open Patent Publication Nos. 2002-300898 and 10-287668 disclose methods for producing polylactic acid from fermented lactic acid products as a starting material. Japanese Laid-Open Patent Publication No. 2002-300898 discloses a method for producing a polylactic acid by esterifying ammonium lactate products from lactic acid fermentation with an alcohol and polycondense them, and then producing lactides and polymerizing them. Japanese Laid-Open Patent Publication No. 10-287668 discloses a method for producing lactide by heating ammonium lactate under reduced pressure, and a method for producing a polylactic acid by ammonia evaporation and dehydratively condensation-polymerization. All of these methods are described as polymerization methods without converting fermented lactic acid products (ammonium lactate salt) from a salt form into a free form. Ammonium lactate is azeotropically dehydrated with xylene to produce polylactic acid, and then polylactic acid with a weight-average molecular weight of 70000 is treated with methylene chloride and methanol for crystallization.

In conventional methods for separating a lactic acid component from a lactic acid fermentation liquor, it is required to separate and purify the lactic acid component by causing a reaction by adding a further reaction reagent, for example, an alcohol such as butanol or pentanol, or a calcium salt such as calcium hydroxide or calcium carbonate. Thus, except for the case of obtaining lactic acid esters or calcium lactate as a final target product, the further reagents may be used with increase in the number of steps, the cost of agents, and the possibility of incorporation of concomitant chemical substances or impurities. For example, when a separated lactic acid component is used as a starting material of chemicals such as polylactic acid or polyester polyol, it is required to separate lactic acid esters produced in the reaction by distillation, and then hydrolyze them to lactic acid as the pre-reaction form. The resultant alcohols are required to be removed since alcohols cannot be contained in the final product.

In the separation method using electrodialysis, there are a concern about the life and fouling of the membranes used. Furthermore, a lactic acid fermentation liquor may contain not only lactic acid, but also organic components such as proteins and surfactants and inorganic components such as salts of phosphoric acid, sulfuric acid, acetic acid, and citric acid, as nutrients and medium components for lactic acid bacteria. Thus, contamination of the membranes is severer, and maintenance of the membranes leads to an increase in the cost. In addition, salts derived from medium components in the fermentation liquor, as well as the lactate salts, are concentrated by dialysis, and thus the precision of separation and the purity of the lactate salt are lowered.

SUMMARY OF THE INVENTION

According to the present invention made in view of these problems, it is intended to provide a method for separating a lactic acid component from a lactic acid fermentation liquor, which does not require reaction reagents, which cause an increase in the cost or incorporation of impurities, or consumables such as separation membranes, which are not contained in a final product, and which includes a reduced number of steps.

The present invention provides a method for separating a lactic acid component, comprising the steps of:

adding at least one solvent selected from the group consisting of toluene, xylene, mesitylene, ethylbenzene, methanol, ethanol, propanol, butanol, and mineral spirit, to a lactic acid fermentation liquor with a pH of 4.8 or less; and extracting a lactic acid component from the solvent added fermentation liquor, at a temperature ranging from room temperature to the boiling point of the solvent.

The present invention also provides a method for separating a lactic acid component, comprising the steps of:

adding at least one solvent selected from the group consisting of toluene, xylene, mesitylene, ethylbenzene, methanol, ethanol, propanol, butanol, and mineral spirit, to a lactic acid fermentation liquor with a pH of 4.8 or less;

heating the solvent added fermentation liquor to azeotropically dehydrate the fermentation liquor; and extracting a lactic acid component from the dehydrated fermentation liquor, at a temperature ranging from room temperature to the boiling point of the solvent.

The present invention further provides a method for separating a lactic acid component, comprising the steps of:

heating a lactic acid fermentation liquor with a pH of 4.8 or less to a temperature of not higher than 100° C. under reduced pressure to dehydrate the fermentation liquor;

adding at least one solvent selected from the group consisting of toluene, xylene, mesitylene, ethylbenzene, methanol, ethanol, propanol, butanol, and mineral spirit, to the dehydrated fermentation liquor; and extracting a lactic acid component from the solvent added fermentation liquor, at a temperature ranging from room temperature to the boiling point of the solvent.

The present invention further provides a method for producing oligo (lactic acid) from a lactic acid fermentation liquor, comprising the steps of:

adding at least one solvent selected from the group consisting of toluene, xylene, mesitylene, ethylbenzene, and mineral spirit, to a lactic acid fermentation liquor with a pH of 4.8 or less;

heating the solvent added fermentation liquor for azeotropy and then to a temperature ranging from the azeotropic point of the solvent and water to the boiling point of the solvent, whereby the fermentation liquor is dehydrated and a lactic acid component in the fermentation liquor is condensed to produce oligo (lactic acid) with a weight-average molecular weight of not greater than 5000; and heating the fermentation liquor which contains the oligo (lactic acid) to a temperature ranging from 60° C. to the boiling point of the solvent to extract the oligo (lactic acid) from the fermentation liquor.

The present invention further provides a method for producing a oligo (lactic acid) from a lactic acid fermentation liquor, comprising the steps of:

heating a lactic acid fermentation liquor with a pH of 4.8 or less to a temperature ranging from 100 to 150° C. under reduced pressure to produce oligo (lactic acid) with a weight-average molecular weight of at least 300 but not greater than 1000 by dehydration-condensation; and adding at least one solvent selected from the group consisting of toluene, xylene, mesitylene, ethylbenzene, and mineral spirit, to the fermentation liquor which contains the oligo (lactic acid); and heating the solvent added fermentation liquor which contains the oligo (lactic acid) to a temperature ranging from 60° C. to the boiling point of the solvent to extract the oligo (lactic acid) from the fermentation liquor.

The present invention further provides a method for producing oligo (lactic acid) from a lactic acid fermentation liquor, comprising the steps of:

heating a lactic acid fermentation liquor with a pH of 4.8 or less to a temperature ranging from 100 to 150° C. under reduced pressure to produce oligo (lactic acid) with a weight-average molecular weight of at least 300 but not greater than 1000 by dehydration-condensation; and washing the fermentation liquor which contains the oligo (lactic acid) with water to separate and collect the oligo (lactic acid) from the fermentation liquor.

In an embodiment, cells are removed from the lactic acid fermentation liquor.

Furthermore, the present invention provides an apparatus for separating a lactic acid component from a lactic acid fermentation liquor, comprising:

starting material supply means for supplying a lactic acid fermentation liquor with a pH of 4.8 or less;

solvent supply means for supplying a solvent selected from the group consisting of a lactic acid component extracting solvent and a washing solvent, the lactic acid component extracting solvent being at least one solvent selected from the group consisting of toluene, xylene, mesitylene, ethylbenzene, methanol, ethanol, propanol, butanol, and mineral spirit, and the washing solvent being water;

a reaction vessel that retains the supplied lactic acid fermentation liquor and solvent with agitation; and lactic acid component separating and collecting means for separating and collecting a lactic acid component from the reaction vessel.

In an embodiment, the apparatus further comprises heating means for heating the reaction vessel.

In a further embodiment, the apparatus further comprises cooling means for condensing a vapor obtained from evaporation out of the reaction vessel.

In a still further embodiment, the apparatus further comprises liquid separating means for subjecting a liquid obtained from condensation by the cooling means to gravity separation for refluxing a liquid with a lower specific gravity to the reaction vessel and discharging water with a higher specific gravity.

In a different embodiment, the apparatus further comprises decolorizing means for decolorizing a liquid collected by the lactic acid component separating and collecting means.

According to the present invention, a lactic acid component can be separated from a lactic acid fermentation liquor with a simple process, at a low cost, and without incorporation of impurities.

BRIEF DESCRIPTION OF THE DRAWING

The drawing is a schematic view of a preferred embodiment of an appartus according to the present invention.

BEST MODE FOR CARRYING OUT THE INVENTION

To complete the present invention, the pH of the lactic acid fermentation liquor has been focused on for the separation of a lactic acid component therefrom. The present invention is based on the findings that at a lower value of pH, lactate ion become lactic acid due to shift of dissociation equilibrium, or the condensation reaction of lactic acid is accerelated to form oligomers, thereby facilitating extraction of the lactic acid component with a solvent. Herein, the lactic acid component refers to lactic acid and/or oligo (lactic acid).

Lactic Acid Fermentation Liquor

Herein, a lactic acid fermentation liquor refers to an aqueous solution containing lactic acid produced from carbon sources such as glucose that can be assimilated in fermentation by microorganisms such as lactic acid bacteria. A lactic acid fermentation liquor may contain cells of microorganisms such as lactic acid bacteria, lactic acid produced by fermentation, a carbon source such as glucose that has not been assimilated, byproducts (acetic acid, formic acid, etc.), medium components as nutrients for the bacteria, and the like.

Lactic acid bacteria may be classified into four types, namely bifidobacteria, *enterococcus* bacteria, *lactobacillus* bacteria, and *streptococcus* bacteria. Lactic acid bacteria include bacteria of the genus *Streptococcus*, the genus *Lactobacillus*, the genus *Bifidohacterium*, the genus *Lactococcus*, the genus *Pediococcus*, and the genus *Leuconostoc*, such as *Streptococcus thermophilus, Streptococcus cremoris, Streptococcus faecalis, Streptococcus lactis, Lactobacillus bulgaricus, Lactobacillus acidophilus, Lactobacillus casei, Lactobacillus delbrueckii, Lactobacillus arabinosus, Lactobacillus caucasicus, Lactobacillus lactis, Lactobacillus Leishmanni, Lactobacillus musicus, Lactobacillus thermophilus, Lactobacillus plantarum, Bifidobacterium bifidum, Bifidobacterium adolescentis, Bifidobacterium longum, Bifidobacterium breve, Bifidobacterium infantis, Lactococcus lactis, Lactococcus cremoris, Pediococcus damnosus*, and *Leuconostoc mesenteroides*. Any bacteria other than those known as lactic acid bacteria also can be used for lactic acid fermentation, as long as they produce lactic acid, and thus such bacteria also may be contained in the lactic acid fermentation liquor. For example, yeast or *Escherichia coli* in which a lactate dehydrogenase (LDH) gene is incorporated can be used. In view of separation of the lactic acid component, bacteria that capable of producing lactic acid alone (homo-lactic fermentation) are preferable.

Medium components that are required vary depending on the type of bacteria, but they include organic components such as amino acids, peptides, vitamins, nucleotides and surfactants, and inorganic components such as salts of phosphoric acid, sulfuric acid, acetic acid and citric acid. For example, MRS (de Man-Rogosa-Sharpe) medium, which is a typical medium for *lactobacillus*, contains peptone, meat extract, yeast extract, potassium phosphate, diammonium citrate, sodium acetate, magnesium sulfate, manganese sulfate, and surfactant, and M17 medium, which is a typical medium for *streptococcus*, contains tryptone, soy peptone, Lab-Lemco powder, yeast extract, ascorbic acid, magnesium sulfate, and disodium glycerophosphate. In addition to the above-mentioned media, synthetic media for lactic acid fermentation can be used in which salts such as ammonium sulfate, dipotassium hydrogen phosphate, potassium dihydrogen phosphate, sodium chloride, magnesium sulfate, calcium chloride, sodium carbonate and L-cysteine hydrochloride, water-soluble vitamins such as thiamine, riboflavin, pyridoxal, cyanocobalamin, L-ascorbic acid, folic acid, nicotinic acid, biotin and pantothenic acid, yeast extract, meat extract, peptone, and the like are mixed as necessary.

Accordingly, the lactic acid fermentation liquor is a mixed aqueous solution that contains many solutes, including lactic acid, and may be colored yellow or orange to brown. In this mixed aqueous solution, the concentration of lactic acid may be approximately 10 to 150 g/L.

In the method according to the present invention, prior to separation of the lactic acid component, cells of microorganisms are preferably removed from the lactic acid fermentation liquor. When cells are removed in advance, impurities can be reduced in the subsequent extraction. Since cells are insoluble in water, the cells can be removed by allowing the lactic acid fermentation liquor to stand, and then collecting supernatant, which can be used for the method according to the present invention. Furthermore, the cells can be removed not by allowing the lactic acid fermentation liquor to stand, but by subjecting the lactic acid fermentation liquor to centrifugal separation or filtration. With this operation, insoluble matter other than cells, such as contaminants, also can be removed.

The pH of the Lactic Acid Fermentation Liquor

In the process of lactic acid fermentation, the pH of the fermentation liquor is lowered due to the produced lactic acid, thereby lowering the activity of microorganisms. Accordingly, fermentation is usually performed with neutralization with an agent such as sodium hydroxide, ammonia water, potassium hydroxide, calcium hydroxide, or sodium carbonate. The pH may be adjusted to near neutral of 5.0 or more in the process of lactic acid fermentation since many lactic acid bacteria does not exhibit a strong ability for fermentation at a pH of less than 5.0. The pKa of lactic acid is approximately 3.8, and thus, when the lactic acid fermentation liquor is near neutral, lactic acid is present in an almost dissociated state and in the form of lactate ions. According to the chemical species of the agent used for neutralization, there are counterions such as ammonium ions, sodium ions, potassium ions, or calcium ions.

The lactic acid fermentation liquor for use in the method of the present invention has a pH of 4.8 or less. Since the pKa of lactic acid is approximately 3.8, at least 10 mol % or more of lactic acid is present without dissociated and in the form of lactic acid in a lactic acid fermentation liquor with a pH of 4.8. A comparison between the molecular polarities of lactate ion and lactic acid shows that lactic acid has a lower polarity than lactate ion, and thus can be more easily dissolved in a solvent other than water. Furthermore, even if the content rate of lactic acid is reduced, dissociation equilibrium can be shifted with extraction of lactic acid to convert lactate ions that may be present in the solution into lactic acid, thereby facilitating extraction of lactic acid. The content rate of lactic acid is preferably increased, and thus, the pH of the lactic acid fermentation liquor is more preferably 3.8 or less. For example, at a pH of 3.8, approximately 50% is present in the form of lactic acid, and thus the extraction efficiency is higher than at a higher pH. A pH of 2.8 or less is still more preferable. At a pH of 2.8 or less, 90% or more is present in the form of lactic acid, and thus the extraction efficiency becomes even higher.

As described above, the pH of the lactic acid fermentation liquor can be usually near neutral of not less than 5.0 in the process of lactic acid fermentation. When the pH of the lactic acid fermentation liquor is greater than 4.8, the pH of the lactic acid fermentation liquor is previously adjusted to 4.8 or less for the method of the present invention. In order to adjust the pH to 4.8 or less, an acid can be added. There is no specific limitation on an acid to be added, but acids such as hydrochloric acid, sulfuric acid, carbonic acid, phosphoric acid, and nitric acid are preferable. Furthermore, the fermentation liquor neutralized with ammonia may be heated for lowering the pH. The temperature and time for heating can be selected as appropriate by a person skilled in the art. For example, the pH can be not greater than 4.8 by heating at 130° C. for 4 hours. Furthermore, the pH can be lowered to 4.3 by heating at 150° C. for 6 hours.

When the pH of the lactic acid fermentation liquor is 4.8 or less, the condensation reaction of lactic acid is facilitated. For example, in the case of that the lactic acid fermentation liquor neutralized with ammonia is heated at 150° C.: when the pH is 6 before pH adjustment, lactic acid is hardly condensed; when the pH is adjusted to 4, 40% of lactic acid can be condensed; and when the pH is adjusted to 2.5, 90% or more of lactic acid can be condensed.

Extraction of the Lactic Acid Component Using the Solvent

In the method according to the present invention, the lactic acid component can be extracted using at least one solvent selected from the group consisting of toluene, xylene, mesitylene, ethylbenzene, methanol, ethanol, propanol, butanol, and mineral spirit, which may be any solvent for industrial use. The amount of solvent added to the fermentation liquor can be selected as appropriate by a person skilled in the art based on the description of the specification. Herein, the solvents are also referred to as "lactic acid component extracting solvents" since these solvents are used for extracting the lactic acid component.

Toluene, xylene, mesitylene, ethylbenzene, and mineral spirit are solvents in which lactic acid or oligo (lactic acid) cannot be dissolved at near room temperature, but lactic acid or oligo (lactic acid) can be dissolved with heating. Therefore, by adding the solvents to the lactic acid fermentation liquor, and heating them preferably with agitation, lactic acid or oligo (lactic acid) can be taken from the lactic acid fermentation liquor. Furthermore, in these solvents, lactic acid or oligo (lactic acid) can be dissolved with heating, but not be dissolved at near room temperature. Therefore, although lactic acid or oligo (lactic acid) is dissolved in the solvents when heated, it becomes insoluble in the solvents and is precipitated when cooled down to near room temperature, thereby facilitating separation and collection of lactic acid or oligo (lactic acid). Accordingly, by using the solvents, lactic acid or oligo (lactic acid), or their mixture can be extracted by heating, and can be readily collected just by cooling down.

The temperature at the extraction can be a temperature ranging from 60° C. to the boiling point of each solvent, and is preferably 150° C. or lower. Since the separation takes advantage of the difference between the solubilities of the lactic acid component and the other components (e.g., medium components) in the lactic acid fermentation liquor, it is desirable that the temperature is such that it can be avoided that the medium components and the like are modified to be water-insoluble. For example, in MRS medium, which is a standard medium for lactic acid bacteria, while the extent of medium components that become water-insoluble by heating at 150° C. for 7 hours is approximately 0.5 wt %, the extent is 1.5 wt % at 160° C., and over 2 wt % at 180° C. Therefore, at a higher temperature, the medium components may be modified to incorporate impurities at the extraction. Thus, it is heated preferably at 150° C. or lower. For example, in the case of xylene, extraction can be performed by heating to a temperature ranging from 60 to 139° C. (the boiling point of m-xylene). Toluene has a boiling point of 110° C., mesitylene has a boiling point of 164.7° C., ethylbenzene has a boiling point of 136° C., and mineral spirit has a boiling point of 150° C. In a case where each solvent is used alone, the heating temperature may be a temperature ranging from 60° C. to the boiling point of the solvent. When the boiling point is higher than 150° C., the heating temperature is preferably 150° C. or lower. In a case where the solvents are used in combination, it is desirable that the temperature is set in consideration of the azeotropic point of the combined solvents and water.

Methanol, ethanol, propanol, and butanol also can be used for extracting the lactic acid component, in consideration of the solubility of lactic acid in these solvents. While lactic acid has a good solubility in methanol, ethanol, propanol, and butanol, the medium components contained in the lactic acid fermentation liquor and the agents for use in neutralization or acidification have a poor solubility in these solvents. The propanol may be either one of 1-propanol (n-propanol) and 2-propanol (isopropanol). The butanol may be any one of 1-butanol (n-butanol), 2-methyl-1-propanol (isobutanol), 2-butanol (sec-butanol), and 2-methyl-2-propanol (tert-butanol).

Here, all of the medium components are soluble in water, but few components among the medium components are soluble in a lower alcohol. For example, in the case of a standard medium M17 for lactic acid fermentation, 100% of the medium components are dissolved in water, but 33.8% of the medium components are soluble in methanol, 5.1% in ethanol, 3.8% in isopropanol, and 4.5% in butanol, that is, the proportion of those that are soluble in these alcohols is small.

Furthermore, the fermentation liquor also may contain salts of an alkali used for neutralization and an acid added for acidification. Examples thereof include ammonium sulfate, sodium sulphate, ammonium chloride, and sodium chloride. Depending on the concentration of lactic acid, these salts may be contained in an amount larger than that of the medium components in the fermentation liquor. These salts are soluble in water, but insoluble or poorly soluble in alcohols such as methanol, ethanol, propanol, or butanol, and thus the amount of soluble matter other than lactic acid is slight.

By adding, to the lactic acid fermentation liquor containing the medium components and the salts of an alkali for neutralization and an acid for acidification in the dissolved states, an alcohol such as methanol, ethanol, propanol, or butanol, which functions as a poor solvent, preferably with agitation, contaminants such as the medium components and the like can become insoluble therein and be precipitated, and the lactic acid component can be collected in the form of liquid.

When the content rate of water in the fermentation liquor is reduced by dehydration in advance, the effect of the alcohol functioning as a poor solvent is increased. Therefore, the increased amount of contaminants is precipitated, and thus the increased extent of solutes other than lactic acid is removed from the fermentation liquor to yield lactic acid with a lower amount of impurities.

Conversely, it is difficult to perform distillation separation and the like after the extraction using an alcohol with 5 or more carbon atoms since it has a high boiling point. For example, while methanol has a boiling point of 65° C., ethanol has a boiling point of 78° C., n-propanol has a boiling point of 97° C., isopropanol has a boiling point of 82° C., isobutanol has a boiling point of 108° C., tertbutanol has a boiling point of 82.5° C., 2-butanol has a boiling point of 100° C., and 1-butanol has a boiling point of 118° C., the boiling points of isomers of pentanol are 112 to 137° C., except that 2-methyl-2-butanol has a boiling point of 102° C. Furthermore, the cost of these alcohols is higher than that of a low molecular weight alcohol.

The temperature at the extraction can be a temperature ranging from room temperature to the boiling point of each solvent. For example, in the case of ethanol, extraction can be performed at a temperature ranging from room temperature to 78° C. Furthermore, in a case where the solvents are used in combination, it is desirable that the temperature is set in consideration of the azeotropic point of the combined solvents and water.

Dehydration of the Lactic Acid Fermentation Liquor by Azeotropy with the Solvent When the lactic acid fermentation liquor is dehydrated, the amount of solvent water is reduced, thereby facilitating dissolution and extraction of the lactic acid component by the solvent. Thus, the dehydration is preferably performed prior to extracting the lactic acid component. The dehydration may be performed simultaneously with extraction of the lactic acid component.

All of the lactic acid component extracting solvents, namely toluene, xylene, mesitylene, ethylbenzene, methanol, ethanol, propanol, butanol, and mineral spirit, are solvents that can form an azeotropic mixture with water. Accordingly, when the lactic acid fermentation liquor to which any of these solvents has been added is heated at least to the azeotropic point of the solvent and water, water can be evaporated out of the reaction system to dehydrate the lactic acid fermentation liquor. The heating is performed preferably with agitation.

Among the lactic acid component extracting solvents, toluene, xylene, mesitylene, ethylbenzene, and mineral spirit, that have a specific gravity smaller than 1 and are water-insoluble, can be separated from water based on the specific gravities. When the solvent is heated together with water to the azeotropic point or higher, then the azeotrope of the water and solvent is evaporated out, and subsequently the azeotrope is cooled down, then the azeotrope is condensed into a liquid. The liquid can be separated into water and the solvent due to the difference between the specific gravities of the solvent and water. Water is removed off, while the solvent is circulated and reused in the reaction system. More specifically, the azeotrope of water and the solvent evaporated out of a reaction vessel by heating is condensed in a cooling tube, introduced into a water separator, and separated into water and the solvent at the lower layer and the upper layer, respectively, based on the difference in the specific gravities. For this purpose, the reaction vessel that has an opening for discharging a vapor is preferably provided with heating means, a cooling tube, and a water separator such as a decanter or a Dean-Stark trap. According to the water separator, water at the lower layer can be removed out of the system, and the solvent at the upper layer can be refluxed and circulated in the reaction vessel. Accordingly, the lactic acid fermentation liquor can be dehydrated without consumption or leakage of the solvent.

The temperature for heating at the azeotropy can be a temperature ranging from the azeotropic point of each solvent and water to the boiling point of the solvent. As described above, at a higher temperature, the medium components may be modified to incorporate impurities at the extraction. Thus, it is heated preferably at 150° C. or lower. For the dehydration, it is preferably heated at the azeotropic point or higher (e.g., preferably 90 to 150° C.) for a time suitable for removing water from the fermentation liquor (e.g., 1 to 5 hours). In the case of toluene, xylene, mesitylene, ethylbenzene, or mineral spirit, lactic acid or oligo (lactic acid), or a mixture of lactic acid and oligo (lactic acid) can be dissolved in these solvents and thus collected.

Furthermore, in the case of alcohols of methanol, ethanol, propanol, and butanol, after the lactic acid fermentation liquor is azeotropically dehydrated, these alcohols may be used to dissolve and collect lactic acid. The lactic acid fermentation liquor may be azeotropically dehydrated in a batch with addition of the alcohol in an excessive amount relative to the amount of water in the lactic acid fermentation liquor, to dissolve lactic acid in the remaining alcohol and collect it. Alternatively, the lactic acid fermentation liquor may be azeotropically dehydrated with continuous addition of the alcohol, to dissolve lactic acid in an added alcohol after the azeotropical dehydration and collect it. As the alcohol for addition to the lactic acid fermentation liquor, an alcohol may be separated from the azeotropic mixture and added again to the lactic acid fermentation liquor, or alternatively an alcohol may be newly added.

Dehydration of the Lactic Acid Fermentation Liquor by Heating under Reduced Pressure The dehydration of the lactic acid fermentation liquor as described above may be performed also by heating under reduced pressure.

The heating temperature is not higher than 100° C., preferably 40 to 100° C. At a temperature of higher than 100° C., the polymerization of lactic acid may be developed in the fermentation liquor. At a temperature of lower than 40° C., the vapor pressure is lower than 55 mmHg, and the speeds of dehydration and drying considerably may be lowered even under the reduced pressure.

The pressure is preferably reduced to 1 to 100 torr (i.e., approximately 133 Pa to approximately 13300 Pa). At a pressure of higher than 100 torr (approximately 13300 Pa), the time required for dehydration and drying may become longer even with heating. At a pressure of lower than 1 torr (approximately 133 Pa), not only water but also some of lactic acid may be removed by evaporation.

For dehydration of the lactic acid fermentation liquor, it is preferable that the heating temperature is not higher than 100° C., preferably 40 to 100° C., and the pressure is reduced to 1 to 100 torr (i.e., approximately 133 Pa to approximately 13300 Pa). The time for heating under reduced pressure can be determined as appropriate according to the heating temperature and the pressure after reduction. The heating under reduced pressure may be performed while changing the heating temperature and the pressure after reduction several times in a stepwise manner. For example, the lactic acid fermentation liquor can be heated to 50° C., and kept under a reduced pressure of 10 torr (approximately 1330 Pa) for 2 hours, and then under a reduced pressure of 5 torr (approximately 670 Pa) for 2 hours for dehydration.

Production of the Oligo (Lacetic Acid) by Azeotropy with the Solvent (Dehydration-Condensation)

With development of the dehydration of the lactic acid fermentation liquor, the condensation reaction of lactic acid can be developed to produce oligo (lactic acid). Since the oligomerized lactic acid has a further lowered polarity, the difference between the solubilities of the lactic acid and the other components, including medium, in the fermentation liquor is increased, thereby facilitating extraction of lactic acid using toluene, xylene, mesitylene, ethylbenzene, and mineral spirit, among the lactic acid component extracting solvents.

Since there are a carboxyl group and a hydroxyl group in one molecule of lactic acid, lactic acids can be homopolymerized by condensation. By discharging water from the polymerization out of the system, the degree of polymerization can be further increased. According to the present invention, such a polymerization of lactic acid is preferable that the weight-average molecular weight is not greater than 5000. At weight-average molecular weight of greater than 5000, the solubility may be lowered in the solvent when heated. Furthermore, it takes a considerably longer time for dehydration-condensation to obtain a weight-average molecular weight of greater than 5000 than that for extraction or dehydration. In the case, the medium components and the like in the fermentation liquor may be deteriorated with heating to modify their solubility, and thus the separation by extraction may be poorly performed.

Also in a dehydration-condensation reaction, the temperature for heating at the azeotropy can be a temperature ranging from the azeotropic point of each solvent and water to the boiling point of the solvent. It is more important to separate oligo (lactic acid) from the other components (e.g., medium components) in the lactic acid fermentation liquor based on the solubilities, rather than to increase the degree of polymerization of lactic acid. More specifically, a difference is to be provided between the solubilities of a lactic acid component and the other components (e.g., medium components) in the lactic acid fermentation liquor by oligomerizing lactic acid. Accordingly, it is desirable that the temperature is such that it can be avoided that the medium components and the like would be modified to be insoluble in water. At a higher temperature, the medium components may be modified to be incorporated as impurities at the extraction. Thus, it is heated preferably at 150° C. or lower. For the dehydration-condensation, it is preferably heated at the azeotropic point or higher (e.g., preferably 90 to 150° C.) for a time suitable for removing water from the fermentation liquor (e.g., 1 to 5 hours), and while keeping a temperature ranging from the azeotropic point to the boiling point of the solvent (note that the temperature is 150° C. or lower), heated for a time suitable for producing an oligomer with a weight-average molecular weight of not greater than 5000 (e.g., 5 to 24 hours). By further applying the heating on a lactic acid fermentation liquor in which the content rate of water is reduced by dehydration, the condensation reaction of lactic acid can be developed to produce oligo (lactic acid).

The oligo (lactic acid) produced by dehydration-condensation is extracted using the lactic acid component extracting solvents (i.e., at least one solvent selected from the group consisting of toluene, xylene, mesitylene, ethylbenzene, and mineral spirit) as described above. In the process of heating (e.g., heating to the boiling point of the solvent) for the dehydration-condensation reaction using the solvent, the extraction process may be performed simultaneously.

Production of the Oligo (Lactic Acid) by Heating under Reduced Pressure (Dehydration-Condensation)

The oligomerization of lactic acid may be performed by heating under reduced pressure. The temperature for heating is preferably in a range of 100 to 150° C. At a temperature for heating of lower than 100° C., the polymerization reactivity of lactic acid may be poorer and thus the extent for conversion of lactic acid to oligomer may be lower. At a temperature for heating of higher than 150° C., the medium components may be deteriorated as described above.

In the case of polymerization by heating under reduced pressure, lactide may be generated during the polymerization of lactic acid. Lactide is generated via the depolymerization reaction of the oligo (lactic acid), and may be an impurity in which two molecules of lactic acid are cyclically associated. In particular, at a higher temperature, or at a higher degree of vacuum, lactide would be generated, and the generated lactide may be sublimated out of the system, thereby lowering the yield of oligo (lactic acid). Accordingly, it is preferable that the heating temperature is 100 to 150° C., and the pressure is reduced to 10 to 100 torr (i.e., approximately 1330 Pa to approximately 13300 Pa). At a pressure of higher than 100 torr (approximately 13300 Pa), the content rate of water may be increased in the system to prevent the condensation. At a pressure of lower than 10 torr (approximately 1330 Pa), lactide may be more generated and sublimated off, thereby lowering the yield of oligo (lactic acid) for separation and collection.

The oligo (lactic acid) produced by heating under reduced pressure can be separated and collected from extraction by heating using at least one solvent selected from the group consisting of toluene, xylene, mesitylene, ethylbenzene, and mineral spirit, among the lactic acid component extracting solvents. The temperature at the extraction by heating is as described above.

The oligo (lactic acid) produced by heating under reduced pressure also can be collected as insoluble in water, by washing the lactic acid fermentation liquor subjected to heating under reduced pressure with water, and dissolving the medium components in water and removing them. Distilled water or deionized water is preferably used. The amount of water for use in washing can be selected as appropriate by a person skilled in the art based on the description of the specification. The oligo (lactic acid) produced by heating under reduced pressure is insoluble in water, but the medium components and the like in the lactic acid fermentation liquor are soluble in water. Accordingly, when the lactic acid fermentation liquor is washed with water (e.g., water is added to the lactic acid fermentation liquor, the mixture is agitated, followed by under solid-liquid separation such as still standing or centrifugal separation), only the medium components are dissolved in water, and thus the oligo (lactic acid), which is insoluble in water, can be separated and collected. The temperature of water at washing can be adjusted in a range from room temperature to the boiling point of water (100° C.). It should be noted that the medium components recovered by washing with water can be used again in a medium for the fermentation.

In the case of polymerization by heating under reduced pressure, the weight-average molecular weight of the obtained oligo (lactic acid) is preferably at least 300 but not greater than 1000. At weight-average molecular weight of greater than 1000, sublimation lactide may be generated via depolymerization, thereby lowering the yield of oligo (lactic acid). At weight-average molecular weight of less than 300, the solubility in the solvent may be lowered compared with that of 300 or more, thereby lowering the efficiency of extraction by heating. Furthermore, oligo (lactic acid), when the solubility in the solvent is lowered, may be more transferred into water at the water washing, thereby lowering the efficiency of the washing. Accordingly, the heating under reduced pressure is performed preferably at a heating temperature of 100 to 150° C. and a reduced pressure of 20 to 100 torr (i.e., approximately 2700 Pa to approximately 13300 Pa), and in such a manner that the weight-average molecular weight of the produced oligo (lactic acid) is at least 300 but not greater than 1000. The time for the heating under reduced pressure can be determined as appropriate according to the temperature for heating and the pressure after reduction. The heating under reduced pressure may be performed while changing the heating temperature and the pressure after reduction several times in a stepwise manner. For example, the lactic acid fermentation liquor can be heated to 150° C., and kept under atmospheric pressure for 2 hours, under a reduced pressure of 100 torr (approximately 13300 Pa) for 2 hours, and then under a reduced pressure of 30 torr (approximately 4000 Pa) for 2 hours for the dehydration-condensation of lactic acid.

The Separated Lactic Acid Component

The lactic acid component (e.g., lactic acid and oligo (lactic acid)) separated from the lactic acid fermentation liquor through the various processes as described above is collected and can be appropriately used as a starting material for synthesizing compounds such as polylactic acid, polyurethane, or polyol ester.

To a liquid that contains the produced lactic acid or oligo (lactic acid) without cooling down, a catalyst (e.g., tin, tin oxide, toluenesulfonic acid, tin chloride, etc.) can be added, and the mixture can be heated continuously to develop the dehydrative polymerization in the solvent, resulting in polylactic acid of a higher molecular weight. The resultant liquid from extraction using the solvent contains only a small amount of coexisting components such as the fermentation medium, thereby facilitating forming that of a higher molecular weight.

Separation Apparatus

The present invention provides an apparatus for separating a lactic acid component from a lactic acid fermentation liquor. The apparatus includes: starting material supply means for supplying a lactic acid fermentation liquor with a pH of 4.8 or less; solvent supply means for supplying a solvent selected from the group consisting of a lactic acid component extracting solvent and a washing solvent, the lactic acid component extracting solvent being at least one solvent selected from the group consisting of toluene, xylene, mesitylene, ethylbenzene, methanol, ethanol, propanol, butanol, and mineral spirit, and the washing solvent being water; a reaction vessel that retains the supplied lactic acid fermentation liquor and solvent with agitation; and lactic acid component separating and collecting means for separating and collecting a lactic acid component from the reaction vessel. In one embodiment, the apparatus may further include heating means for heating the reaction vessel, and can facilitate the production of oligo (lactic acid) by dehydration or dehydration-condensation in the lactic acid fermentation liquor. The apparatus may further include cooling means for condensing a vapor from evaporation out of the reaction vessel. The apparatus may further include liquid separating means for subjecting a liquid from condensation by the cooling means to gravity separation for refluxing a liquid with a lower specific gravity to the reaction vessel and discharging water with a higher specific gravity.

With this configuration, the solvent can be circulated and reused, by extraction and by heating when heating is performed. Thus, safety and low cost can be achieved without leakage or consumption of the solvent.

Then, an apparatus for separating a lactic acid component from a lactic acid fermentation liquor according to the present invention will be described with reference to FIG. 1, which shows an embodiment. FIG. 1 shows the configuration of an apparatus suitable for a method for separating a lactic acid component by azeotropical dehydration and azeotropical condensation. Note that in order to separate a lactic acid component from a lactic acid fermentation liquor, not all the constituent elements shown in FIG. 1 are required.

A reaction vessel 4 is configured to be capable of retaining a lactic acid fermentation liquor and a solvent, which may be separated from each other when allowed to stand, and agitating to mix the lactic acid fermentation liquor and the solvent with heating if necessary. The reaction vessel 4 may include agitator blades 2 that are rotated by an agitator motor 1. The reaction vessel 4 may further include heating means (e.g., a heater 3) for heating the reaction vessel, if necessary.

Starting material supply means includes a lactic acid fermentation liquor tank and a pH adjusting vessel 5 that is connected to the tank. The Starting material supply means is configured to supply the lactic acid fermentation liquor, pH of which is adjusted to 4.8 or less at the pH adjusting vessel 5, via a liquid sending pump 6 to the reaction vessel 4.

Solvent supply means includes a solvent tank, and is configured to supply the solvent via a liquid sending pump 7 to the reaction vessel 4. In an embodiment where the lactic acid component extracting solvent is used to separate and collect a lactic acid component, the solvent supply means includes a solvent tank that contains at least one solvent selected from the group consisting of toluene, xylene, mesitylene, ethylbenzene, methanol, ethanol, propanol, butanol, and mineral spirit. In a case where two or more types of solvents are used, the solvent supply means may be configured to send these solvents separately, or may be configured to send these solvents in a mixed state.

In an embodiment where a lactic acid fermentation liquor subjected to pH adjustment and heating under reduced pressure is washed with water inside the reaction vessel 4, the solvent supply means may supply water as a washing solvent to the reaction vessel 4.

In the apparatus according to the present invention, as the solvent supply means, a solvent tank that supplies a lactic acid component extracting solvent and a solvent tank that supplies water may be arranged in parallel.

Lactic acid component separating and collecting means refers to any means for separating and collecting a lactic acid component after stopping agitation in the reaction vessel 4. In order to separate a lactic acid component from a lactic acid fermentation liquor, separation by stopping agitation of the agitator blades 2 arranged in the reaction vessel 4 is used. When the lactic acid component extracting solvent is used to separate and collect a lactic acid component, the lactic acid component can be contained in a separated liquid with a lower specific gravity (the upper layer). When water is used as the washing solvent to separate and collect a lactic acid component, the lactic acid component cannot be contained in a separated liquid with a lower specific gravity (the upper layer), but the lactic acid component can be precipitated.

In an embodiment where the lactic acid component extracting solvent is used to separate and collect a lactic acid component, a liquid which contains the lactic acid component, which is separated by stopping agitation in the reaction vessel, is collected for separation and collection of the lactic acid component. For example, a pipe 14 is provided at the upper portion of the reaction vessel 4 and connected to a purifier 13. More specifically, agitation by the agitator blades 2 arranged in the reaction vessel 4 is stopped, and a separated liquid with a lower specific gravity (the upper layer) by stopping the agitation is sent from the upper portion of the reaction vessel 4 via the pipe 14 to the purifier 13. At the purifier 13, a lactic acid component dissolved in the supplied liquid can be separated and collected.

At the purifier 13, in order to separate and collect a lactic acid component, either solid-liquid separation or solvent removal by evaporation may be used according to the solvent used to extract the lactic acid component.

When toluene, xylene, mesitylene, ethylbenzene, or mineral spirit is used as the lactic acid component extracting solvent, a liquid collected in the purifier 13 is cooled down to precipitate a dissolved component in the liquid, and subjected to a separation technique such as still standing or centrifugal separation. The solid component, which has been dissolved, and liquid component are collected, while the solvent of supernatant can be circulated into the reaction vessel. In this case, the purifier 13 preferably has cooling means (not shown), and thus the solute of the content in the purifier 13 is precipitated by this cooling function, and the supernatant of the content in the purifier 13 is introduced via a pipe 15 into a solvent supply line. As a valve used for a discharge pipe (not shown) of the purifier 13, a ball valve is preferable because a slurry or solid component flows therethrough.

When methanol, ethanol, propanol, or butanol is used as the lactic acid component extracting solvent, the solvent, which is contained in a liquid collected in the purifier 13, is removed by evaporation, and the liquid from which the solvent has been removed can be collected from the purifier 13. In this case, the purifier 13 preferably has an evaporator or the like device (not shown), and thus, at the purifier 13, while the extracting solvent can be removed off from the collected liquid by the device, the desired solute can be collected in the form of liquid. Also, means for solid-liquid separation on the collected liquid using a separation technique such as still standing or centrifugal separation may be provided. If insolubles are present in the collected liquid, the insolubles can be also removed by this means. The solvent removed out of the purifier 13 may be liquefied through the pipe 15 to be introduced into the solvent supply line. Accordingly, the pipe 15 preferably includes a device (e.g., cooling device) (not shown) that liquefies an evaporated solvent.

A discharge pipe 16 is provided at the vessel bottom portion of the reaction vessel 4, and is configured to be capable of discharging precipitates (e.g., a solid component precipitated by loading an alcohol solvent) or the like in the reaction vessel 4.

In an embodiment where a lactic acid fermentation liquor subjected to pH adjustment and heating under reduced pressure is washed with water, the produced oligo (lactic acid) can be obtained in the reaction vessel 4 while removing a supernatant aqueous solution with a lower specific gravity separated following stopping agitation in the reaction vessel 4. In this embodiment, stopping of agitation of the agitator blades 2 arranged in the reaction vessel 4 is mainly used for collecting a lactic acid component. A pipe provided at the upper portion of the reaction vessel 4 can be used for discharging the separated supernatant aqueous solution with a lower specific gravity (containing dissolved medium components and the like), and a pipe or collecting port (not shown) may be provided at the lower portion or the bottom portion of the reaction vessel 4 such that is configured to be capable of collecting the oligo lactic acid). In this embodiment, the pipe 14 in communication with the purifier 13 may be used as the pipe for discharging the supernatant aqueous solution with a lower specific gravity.

The cooling means is a means for cooling down a vapor that is obtained from evaporation out of the reaction vessel 4 and includes water and the solvent. Examples thereof include water-cooling, air-cooling, evaporative, or other condensers. For example, as a water-cooling condenser, a condenser having the structure of shell-and-tube, double-tube, or the like is used. The liquid separating means is a means by which a liquid obtained from cooling down and condensation by the cooling means is separated into water and the solvent for discharge water and returning the solvent into the system. Examples thereof include water separators such as a decanter and a Dean-Stark trap. More specifically, a condenser 9 and a decanter 10 are connected via a distillation column 8 to the reaction vessel 4. A vapor from the reaction vessel 4 by heating is rectified in the distillation column 8, and then a liquid obtained from cooling down and condensation by the condenser 9 flows down to the decanter 10. In the decanter 10, water and the solvent are separated to form two layers due to the difference in specific gravities. The upper solvent layer is refluxed via a U-tube 11 to the distillation column 8, and the lower water layer is discharged by discharge means (not shown). Furthermore, the liquid obtained from condensation in the distillation column 8 flows down, and then is circulated via a U-tube 12 to the reaction vessel 4.

The distillation column 8 may be an empty column, or may be filled with Raschig rings, Lessing rings such as Dixon packings, Pall rings, saddles such as McMahon packings, Sulzer packings, or other fillers. Furthermore, the outer wall of the distillation column 8 may be heat-sealed with glass wool or the like.

Since a mixture of water and the solvent is cooled down in the condenser 9, the cooling is performed preferably at 0° C. or higher and room temperature or lower. The cooling is performed more preferably at 2 to 10° C. in order to increase the ability to cool down and condense into a liquid. Any condenser may be used as the condenser 9, as long as the vapor pipe can be cooled down from the outside at its contact face, and examples thereof include a Liebig condenser, an Allihn condenser, and a Liebig-Graham condenser.

The decanter 10 may be cooled down in order to increase the efficiency of separation of a mixed liquid based on the difference in specific gravities.

The apparatus may further include decolorizing means for decolorizing a liquid collected by the lactic acid component separating and collecting means. An absorbent such as activated carbon or activated clay may be used for the decolorization. More specifically, the decolorizing means includes: a column which is filled with the absorbent and through which the collected liquid can pass; and loading the absorbent into the collected liquid followed by separating and removing the loaded absorbent. For example, the liquid can be decolorized by passing through the column. Alternatively, the liquid can be decolorized by being mixed with the absorbent, and subjected to solid-liquid separation such as filtration or centrifugal separation.

The containers and the pipes are made of, for example, stainless steel, glass, or resin such as Teflon (registered trade name).

Then, the operating process of a method for separating a lactic acid component using the apparatus will be described.

In one embodiment, a lactic acid fermentation liquor, pH of which is adjusted to 4.8 or less by addition of an acid at the pH adjusting vessel 5, is supplied via the liquid sending pump 6 to the reaction vessel 4. A solvent is supplied from the solvent tank via the liquid sending pump 7 to the reaction vessel 4. In the reaction vessel 4, the lactic acid fermentation liquor and the solvent are suspended by agitation of the agitator blades 2 that are rotated by the agitator motor 1. If necessary, the content in the reaction vessel 4 is heated by the heater 3. Subsequently, the agitation is stopped and the content is allowed to stand, while continuing heating if heating is performed. The resultant supernatant of the content in the reaction vessel 4 is supplied via the pipe 14 to the purifier 13. The lactic acid component in the content is separated and collected at the purifier 13. In this manner, the lactic acid component is separated and collected from the lactic acid fermentation liquor.

In an embodiment where methanol, ethanol, propanol, or butanol is used as the lactic acid component extracting solvent in order to collect the lactic acid component in the purifier 13, the solvent is removed by evaporation, by heating to a temperature ranging from room temperature to the boiling point of the solvent, while the pressure is reduced by a vacuum pump (not shown) attached to the purifier 13, for example, to 0.5 to 500 torr (i.e., approximately 67 Pa to approximately 67000 Pa). Since methanol, ethanol, and propanol have a high vapor pressure, the solvent also can be removed by evaporation, by heating at least to the boiling point of the solvent under ambient pressure. The remaining liquid is collected to obtain a lactic acid component in the form of liquid. If insolubles are present in the collected liquid, solid-liquid separation may be performed on the collected liquid using a separation technique such as still standing or centrifugal separation, and thus, a transparent liquid can be collected. The solvent removed off by evaporation may be liquefied through the pipe 15, to which a cooling device is attached if necessary, and supplied again as the extracting solvent via the liquid sending pump 7 to the reaction vessel 4.

In an embodiment where toluene, xylene, mesitylene, ethylbenzene, or mineral spirit is used as the lactic acid component extracting solvent, the content in the purifier 13 is cooled down by the cooling device (not shown) to precipitate the solute of the content, and the precipitated lactic acid component is collected. In this manner, the lactic acid component is separated from the lactic acid fermentation liquor. Furthermore, the supernatant of the content in the purifier 13 is introduced via the pipe 15 into the solvent supply line, and sent back to the reaction vessel 4.

In a different embodiment, a lactic acid fermentation liquor, pH of which is adjusted to 4.8 or less by addition of an acid at the pH adjusting vessel 5, is supplied via the liquid sending pump 6 to the reaction vessel 4. A solvent is supplied from the solvent tank via the liquid sending pump 7 to the reaction vessel 4. In the reaction vessel 4, the lactic acid fermentation liquor and the solvent are suspended by agitation of the agitator blades 2 that are rotated by the agitator motor 1. The content in the reaction vessel 4 is heated by the heater 3. When the content in the reaction vessel 4 is heated at least to the azeotropic point of water and the solvent (e.g., 90° C. or higher), the content starts to be evaporated. The vapor from evaporation passes through the distillation column 8, and is cooled down and condensed at the condenser 9, and flows down to the decanter 10. The condenser 9 (or the condenser 9 and the decanter 10) is cooled down with circulating chilled water or the like. In the decanter 10, the condensate is separated into the solvent and water at the upper layer and at the lower layer, respectively, due to the difference in specific gravities because the solvent and water are not miscible. The solvent at the upper layer flows back via the U-tube 11 to the distillation column 8. Because of the pipe for the return path of U-shaped, the effect of water removal is further increased. The solvent that has flowed back is refluxed together with a solvent that is refluxed in the distillation column 8, to be refluxed via the U-tube 12 to the reaction vessel 4. The reaction vessel 4 is heated continuously until most of the water in the supplied fermentation liquor is removed, and then the agitation is stopped and the content is allowed to stand while continuing the heating (the heating temperature may be the same or may be changed). The resultant supernatant of the content in the reaction vessel 4 is supplied via the pipe 14 to the purifier 13. A lactic acid component in the content is separated and collected at the purifier 13. The lactic acid component is separated and collected at the purifier 13 as described above.

In an embodiment where methanol, ethanol, propanol, or butanol is used as the lactic acid component extracting solvent, lactic acid can be collected by azeotropically dehydrating the lactic acid fermentation liquor without reflux of the solvent, and then dissolving the azeotropically dehydrated lactic acid fermentation liquor in the solvent. This is because the solvent and water are miscible and cannot be separated even at the decanter 10. The lactic acid fermentation liquor may be azeotropically dehydrated in a batch by addition of the alcohol in an excessive amount relative to the amount of water in the lactic acid fermentation liquor, and then in the remaining alcohol, lactic acid may be dissolved for collection. Alternatively, the lactic acid fermentation liquor may be azeotropically dehydrated by continuous addition of the alcohol, and then in an alcohol added after the azeotropical dehydration, lactic acid may be dissolved for collection. As the alcohol for addition to the lactic acid fermentation liquor, an alcohol may be separated from the azeotropic mixture and added again to the lactic acid fermentation liquor, or alternatively an alcohol may be newly added.

In a still different embodiment, a lactic acid fermentation liquor, pH of which is adjusted to 4.8 or less by addition of an acid at the pH adjusting vessel 5, is supplied via the liquid sending pump 6 to the reaction vessel 4. Then, the reaction vessel 4 is heated by the heater 3 for an appropriate time (preferably 1 to 10 hours) to a temperature of not higher than 100° C., preferably to a temperature of 40 to 100° C., while the pressure in the reaction vessel 4, the distillation column 8, and pipes connecting these constituent elements is reduced, for example, to 1 to 100 torr (i.e., approximately 133 Pa to approximately 13300 Pa), by the vacuum pump (not shown) connected to the condenser 9. The content in the reaction vessel 4 starts to be evaporated. The vapor from evaporation passes through the distillation column 8, and is cooled down and condensed at the condenser 9. The water from condensation is discharged from the pipe. The condenser 9 is cooled down with circulating chilled water or the like. Accordingly, the lactic acid fermentation liquor in the reaction vessel 4 is dehydrated. Subsequently, the solvent is supplied from the solvent tank via the liquid sending pump 7 to the reaction vessel 4. In the reaction vessel 4, the dehydrated lactic acid fermentation liquor and the solvent are agitated by the agitator blades 2 that are rotated by the agitator motor 1 for an appropriate time (preferably 1 to 5 hours), under application of heat to a temperature ranging from room temperature to the boiling point of the solvent (note that the temperature is not higher than 150° C.) with the heater 3 if necessary. The agitation is stopped and the content is allowed to stand. The resultant supernatant of the content in the reaction vessel 4 is supplied via the pipe 14 to the purifier 13. The lactic acid component in the content is separated and collected at the purifier 13. The lactic acid component is separated and collected at the purifier 13 as described above.

In a further different embodiment, a lactic acid fermentation liquor, pH of which is adjusted to 4.8 or less by addition of an acid at the pH adjusting vessel 5, is supplied via the liquid sending pump 6 to the reaction vessel 4. A solvent is supplied from the solvent tank via the liquid sending pump 7 to the reaction vessel 4. In the reaction vessel 4, the lactic acid fermentation liquor and the solvent are suspended by agitation of the agitator blades 2 that are rotated by the agitator motor 1. The content of the reaction vessel 4 is heated by the heater 3. When the content in the reaction vessel 4 is heated at least to the azeotropic point of water and the solvent (e.g., 90° C. or higher), the content starts to be evaporated. The vapor from evaporation passes through the distillation column 8, and is cooled down and condensed at the condenser 9, and flows down to the decanter 10. The condenser 9 (or the condenser 9 and the decanter 10) is cooled down with circulating chilled water or the like. In the decanter 10, the condensate is separated into the solvent and water at the upper layer and at the lower layer, respectively, due to the difference in specific gravities because the solvent and water are not miscible. The solvent at the upper layer flows back via the U-tube 11 to the distillation column 8. Because of the pipe for the return path of U-shaped, the effect of water removal is further increased. The solvent that has flowed back is refluxed together with a solvent that is refluxed in the distillation column 8, to be refluxed via the U-tube 12 to the reaction vessel 4. The reaction vessel 4 is heating continuously until most of the water in the supplied fermentation liquor is removed, and then the temperature for heating is increased to the boiling point of the solvent (note that the temperature is not higher than 150° C.), and the heating is further continued. The heating and agitation are performed for an appropriate time (preferably 5 to 24 hours), and then the agitation is stopped and the content is allowed to stand while continuing the heating. The resultant supernatant of the content in the reaction vessel 4 is supplied via the pipe 14 to the purifier 13. The lactic acid component in the content is separated and collected at the purifier 13. The lactic acid component is separated and collected at the purifier 13 as described above.

In this embodiment, toluene, xylene, mesitylene, ethylbenzene, or mineral spirit may be used as the solvent. Here, the separation and collection of the lactic acid component at the purifier 13 will be described. The content in the purifier 13 is cooled down by the cooling device (not shown) to precipitate the solute of the content, and the precipitated oligo (lactic acid) is collected. In this manner, the oligo (lactic acid) produced by dehydration-condensation of the lactic acid is separated and collected from the lactic acid fermentation liquor. Furthermore, the supernatant of the content in the purifier 13 is introduced via the pipe 15 into the solvent supply line, and is sent back to the reaction vessel 4.

In a still further different embodiment, a lactic acid fermentation liquor, the pH of which is adjusted to 4.8 or less by addition of an acid at the pH adjusting vessel 5, is supplied via the liquid sending pump 6 to the reaction vessel 4. Then, the reaction vessel 4 is heated by the heater 3 for an appropriate time (preferably 5 to 24 hours) to a temperature ranging from 100 to 150° C., while the pressure in the reaction vessel 4, the distillation column 8, and pipes connecting these constituent elements is reduced, for example, to 10 to 100 torr (i.e., approximately 1330 Pa to approximately 13300 Pa), by the vacuum pump (not shown) connected to the condenser 9. The content in the reaction vessel 4 starts to be evaporated. The vapor from evaporation passes through the distillation column 8, and is cooled down and condensed at the condenser 9. The water from condensation is discharged from the pipe. The condenser 9 is cooled down with circulating chilled water or the like. Thus, the lactic acid fermentation liquor in the reaction vessel 4 is subjected to dehydration-condensation. Subsequently, the solvent is supplied from the solvent tank via the liquid sending pump 7 to the reaction vessel 4. In the reaction vessel 4, the lactic acid fermentation liquor subjected to dehydration-condensation and the solvent are agitated by the agitator blades 2 that are rotated by the agitator motor 1 for an appropriate time (preferably 1 to 5 hours), under application of heat to a temperature ranging from 60° C. to the boiling point of the solvent (note that the temperature is not higher than 150° C.) with the heater 3. The agitation is stopped and the content is allowed to stand while continuing the heating. The resultant supernatant of the content in the reaction vessel 4 is supplied via the pipe 14 to the purifier 13. The lactic acid component in the content is separated and collected at the purifier 13. The lactic acid component is separated and collected at the purifier 13 as described above.

In this embodiment, toluene, xylene, mesitylene, ethylbenzene, or mineral spirit may be used as the solvent. Here, the separation of the lactic acid component at the purifier 13 will be described. The content in the purifier 13 is cooled down by the cooling device (not shown) to precipitate the solute of the content, and the precipitated oligo (lactic acid) is collected. In this manner, the oligo (lactic acid) produced by dehydration-condensation of the lactic acid is separated and collected from the lactic acid fermentation liquor. Furthermore, the supernatant of the content liquid in the purifier 13 is introduced via the pipe 15 into the solvent supply line, and is sent back to the reaction vessel 4.

The aforementioned apparatus can be used also in a case where for the production of the oligo (lactic acid), the fermentation liquor is heating under reduced pressure without using the solvent, and is washed with water. A lactic acid fermentation liquor, pH of which is adjusted to 4.8 or less by addition of an acid at the pH adjusting vessel 5, is supplied via the liquid sending pump 6 to the reaction vessel 4. Then, the reaction vessel 4 is heated by the heater 3 for an appropriate time (preferably 5 to 24 hours) to a temperature ranging from 100 to 150° C., while the pressure in the reaction vessel 4, the distillation column 8, and pipes connecting these constituent elements is reduced, for example, to 20 to 100 torr (i.e., approximately 2700 Pa to approximately 13300 Pa), by the vacuum pump (not shown) connected to the condenser 9. The content in the reaction vessel 4 starts to be evaporated. The vapor from evaporation passes through the distillation column 8, and is cooled down and condensed at the condenser 9. The water from condensation is discharged from the pipe. The condenser 9 is cooled down with circulating chilled water or the like. Thus, the lactic acid fermentation liquor in the reaction vessel 4 is subjected to dehydration-condensation. Subsequently, water is supplied from the water tank via the liquid sending pump 7 to the reaction vessel 4. In the reaction vessel 4, the lactic acid fermentation liquor subjected to dehydration-condensation and the supplied water are agitated by the agitator blades 2 that are rotated by the agitator motor 1 for an appropriate time (preferably 0.5 to 5 hours), under application of heat to a temperature up to the boiling point of water with the heater 3 if necessary. Subsequently, the agitation is stopped and the content is allowed to stand while continuing heating if heating is performed. A supernatant aqueous solution with a lower specific gravity is discharged via a pipe (that also may be the pipe 14). With this procedure, the produced oligo (lactic acid) can be separated and collected in the reaction vessel 4. The produced oligo (lactic acid) also may be further polymerized by heating under reduced pressure in the reaction vessel 4. After washing with water in the reaction vessel 4 to separate and collect the oligo (lactic acid), this oligo (lactic acid) may be dissolved again using the lactic acid component extracting solvent for separation and collection in the purifier 13.

In this manner, a lactic acid component can be easily separated only by using the solvent, and agitating the lactic acid fermentation liquor, and if necessary, adjusting the temperature and/or reducing the pressure, after adjusting the pH of the lactic acid fermentation liquor. Since only the solvent supplied from the solvent tank is used, a lactic acid component can be extracted with few impurities and at low cost. Furthermore, the solvent used for extraction can be circulated and used continuously, and thus a low-cost and safe apparatus without consumption or leakage of the solvent can be obtained.

Hereinafter, the present invention will be specifically described using examples, but the technical scope of the present invention is not limited to these examples.

EXAMPLES

Example 1

In a lactic acid fermentation liquid medium that contained 3.5 wt % of standard medium M17 (manufactured by Difco Laboratories) for *streptococcus*, supplemented with 14 wt % of glucose, lactic acid bacteria (streptococcus bacteria) were subjected to lactic acid fermentation in suspension culture while the pH of the medium was adjusted with ammonia to near 6, to obtain 20 g of lactic acid fermentation liquor (pH 6) in which the concentration of ammonium lactate was 10 wt %. The cells of bacteria were removed in advance from the lactic acid fermentation liquor by centrifugal separation. The pH of the lactic acid fermentation liquor was adjusted to 4.8 by addition of sulfuric acid. Subsequently, 50 ml of xylene was added thereto, and the mixture was heated at 130° C. with agitation in a reflux state. One hour later, the agitation was stopped and the mixture was allowed to stand while continuing heating at 130° C., to separate it into two layers. When the upper layer was collected and cooled down to room temperature, precipitation was observed. The precipitation was due to lactic acid, and the yield of the extraction was 10% (see Table 1 below).

Example 2

As in Example 1 above, 20 g of lactic acid fermentation liquor (pH 6) was obtained in which the concentration of ammonium lactate was 10 wt %. The cells of bacteria were removed from the lactic acid fermentation liquor as in Example 1. The pH of the lactic acid fermentation liquor was adjusted to 2.5 by addition of sulfuric acid. Subsequently, 50 ml of xylene was added thereto, and the mixture was heated at 130° C. with agitation in a reflux state. One hour later, the agitation was stopped and the mixture was allowed to stand while continuing heating at 130° C., to separate it into two layers. When the upper layer was collected and cooled down to room temperature, precipitation was observed. The precipitation was due to lactic acid, and the yield of the extraction was 20% (see Table 1 below).

Comparative Example 1

As in Example 1 above, 20 g of lactic acid fermentation liquor (pH 6) was obtained in which the concentration of ammonium lactate was 10 wt %. The cells of bacteria were removed from the lactic acid fermentation liquor as in Example 1. Here, the pH of the lactic acid fermentation liquor was not adjusted. Then, 50 ml of xylene was added to the lactic acid fermentation liquor, and the mixture was heated to 130° C. with agitation. One hour later, the agitation was stopped and the mixture was allowed to stand while continuing heating at 130° C. in a reflux state, to separate it into two layers. When the upper layer was collected and cooled down to room temperature, a small amount of precipitation was observed. The precipitation was due to ammonium lactate, and the yield of the extraction was as slight as 0.6% (see Table 1 below).

Table 1 below collectively shows the results of the extraction by heating the lactic acid fermentation liquor with xylene.

TABLE 1

|  | pH | Condition for reaction | Product | Yield |
|---|---|---|---|---|
| Example 1 | 4.8 | Addition of xylene and reflux at 130° C. | Lactic acid | 10% |
| Example 2 | 25 | Addition of xylene and reflux at 130° C. | Lactic acid | 20% |
| Comparative Example 1 | 6 | Addition of xylene and reflux at 130° C. | Ammonium lactate | 0.6% |

Example 3

As in Example 1 above, 20 g of lactic acid fermentation liquor (pH 6) was obtained in which the concentration of ammonium lactate was 10 wt %. The cells of bacteria were removed from the lactic acid fermentation liquor as in Example 1. The pH of the lactic acid fermentation liquor was adjusted to 4.8 by addition of sulfuric acid. Subsequently, 50 ml of xylene was added thereto, and the mixture was heated to 100° C. with agitation. A vapor was condensed, water from which was removed, and then refluxed, and about 17 g of water was thus removed over approximately 2 hours. Subsequently, the mixture was heated to 130° C. One hour later, the agitation was stopped and the mixture was allowed to stand, to separate it into two layers. When the upper layer was collected and cooled down to room temperature, precipitation was observed. The precipitation was due to lactic acid, and the yield of the extraction was 20% (see Table 2 below).

Example 4

As in Example 1 above, 20 g of lactic acid fermentation liquor (pH 6) was obtained in which the concentration of ammonium lactate was 10 wt %. The cells of bacteria were removed from the lactic acid fermentation liquor as in Example 1. The pH of the lactic acid fermentation liquor was adjusted to 2.5 by addition of sulfuric acid. Subsequently, 50 ml of xylene was added thereto, and the mixture was heated to 100° C. with agitation. A vapor was condensed, water from which was removed, and then refluxed, and about 17 g of water was thus removed over approximately 2 hours. Subsequently, the mixture was heated to 130° C. One hour later, the agitation was stopped and the mixture was allowed to stand, to separate it into two layers. When the upper layer was collected and cooled down to room temperature, precipitation was observed. The precipitation was due to lactic acid, and the yield of the extraction was 35.5% (see Table 2 below).

Comparative Example 2

As in Example 1 above, 20 g of lactic acid fermentation liquor (pH 6) was obtained in which the concentration of ammonium lactate was 10 wt %. The cells of bacteria were removed from the lactic acid fermentation liquor as in Example 1. Here, the pH of the lactic acid fermentation liquor was not adjusted. Then, 50 ml of xylene was added thereto, and the mixture was heated to 100° C. with agitation. A vapor was condensed, water from which was removed, and then refluxed, and about 17 g of water was thus removed over approximately 2 hours. Subsequently, the mixture was heated to 130° C. One hour later, the agitation was stopped and the mixture was allowed to stand, to separate it into two layers. When the upper layer was collected and cooled down to room temperature, precipitation was observed. The precipitation was due to lactic acid, and the yield of the extraction was 3.8% (see Table 2 below).

Table 2 below collectively shows the results of dehydration of the lactic acid fermentation liquor by azeotropy with xylene.

TABLE 2

|  | pH | Condition for reaction | Product | Yield |
|---|---|---|---|---|
| Example 3 | 4.8 | Addition of xylene and reflux at 100° C. followed by heating to 130° C. | Lactic acid | 20% |
| Example 4 | 2.5 | Addition of xylene and reflux at 100° C. followed by heating to 130° C. | Lactic acid | 35.5% |
| Comparative Example 2 | 6 | Addition of xylene and reflux at 100° C. followed by heating to 130° C. | Lactic acid | 3.8% |

Example 5

As in Example 1 above, 20 g of lactic acid fermentation liquor (pH 6) was obtained in which the concentration of ammonium lactate was 10 wt %. The cells of bacteria were removed from the lactic acid fermentation liquor as in Example 1. The pH of the lactic acid fermentation liquor was adjusted to 4.8 by addition of sulfuric acid. Subsequently, 50 ml of xylene was added to thereto, and the mixture was heated to 100° C. with agitation. A vapor was condensed, water from which was removed, and then refluxed, and about 17 g of water was thus removed over approximately 2 hours. Subsequently, the mixture was heated to 139° C. Twenty hours later, the agitation was stopped and the mixture was allowed to stand, to separate it into two layers. When the upper layer was collected and cooled down to room temperature, precipitation was observed. The precipitation was due to oligo (lactic acid), and the yield of the extraction was 46.7%. A determination of the molecular weight by gel permeation chromatography showed that the weight-average molecular weight was 350 (see Table 3 below).

Example 6

As in Example 1 above, 20 g of lactic acid fermentation liquor (pH 6) was obtained in which the concentration of ammonium lactate was 10 wt %. The cells of bacteria were removed from the lactic acid fermentation liquor as in Example 1. The pH of the lactic acid fermentation liquor was adjusted to 2.5 by addition of sulfuric acid. Subsequently, 50 ml of xylene was added thereto, and the mixture was heated to 100° C. with agitation. A vapor was condensed, water from which was removed, and then refluxed, and about 17 g of water was thus removed over approximately 2 hours. Subsequently, the mixture was heated to 139° C. Twenty hours later, the agitation was stopped and the mixture was allowed to stand, to separate it into two layers. When the upper layer was collected and cooled down to room temperature, precipitation was observed. The precipitation was due to oligo (lactic acid), and the yield of the extraction was 63.6%. A determination of the molecular weight by gel permeation chromatography showed that the weight-average molecular weight was 698 (see Table 3 below).

Comparative Example 3

As in Example 1 above, 20 g of lactic acid fermentation liquor (pH 6) was obtained in which the concentration of ammonium lactate was 10 wt %. The cells of bacteria were removed from the lactic acid fermentation liquor as in Example 1. Here, the pH of the lactic acid fermentation liquor was not adjusted. Then, 50 ml of xylene was added to the lactic acid fermentation liquor, and the mixture was heated to 100° C. with agitation. A vapor was condensed, water from which was removed, and then refluxed, and about 17 g of water was thus removed over approximately 2 hours. Subsequently, the mixture was heated to 139° C. Twenty hours later, the agitation was stopped and the mixture was allowed to stand, to separate it into two layers. When the upper layer was collected and cooled down to room temperature, precipitation was observed. The precipitation was due to oligo (lactic acid), and the yield of the extraction was 5%. A determination of the molecular weight by gel permeation chromatography showed that the weight-average molecular weight was 137 (see Table 3 below).

Table 3 below collectively shows the results of dehydration-condensation of the lactic acid fermentation liquor by azeotropy with xylene.

TABLE 3

| | pH | Condition for reaction | Product | Yield |
|---|---|---|---|---|
| Example 5 | 4.8 | Addition of xylene and reflux at 100° C. followed by heating to 139° C. for 20 hrs | Oligo (Lactic acid) M.W. 350 | 46.7% |
| Example 6 | 2.5 | Addition of xylene and reflux at 100° C. followed by heating to 139° C. for 20 hrs | Oligo (Lactic acid) M.W. 698 | 63.6% |
| Comparative Example 3 | 6 | Addition of xylene and reflux at 100° C. followed by heating to 139° C. for 20 hrs | Oligo (Lactic acid) M.W. 137 | 5% |

Example 7

As in Example 1 above, 20 g of lactic acid fermentation liquor (pH 6) was obtained in which the concentration of ammonium lactate was 10 wt %. The cells of bacteria were removed from the lactic acid fermentation liquor as in Example 1. The pH of the lactic acid fermentation liquor was adjusted to 4.8 by addition of sulfuric acid. Subsequently, the lactic acid fermentation liquor was heated to 150° C., and kept under atmospheric pressure for 2 hours, under a reduced pressure of 100 torr (approximately 13300 Pa) for 2 hours, and then under a reduced pressure of 30 torr (approximately 4000 Pa) for 2 hours. Then, 50 ml of xylene was added thereto, and the mixture was heated to 100° C. with agitation. On hour later, the agitation was stopped and the mixture was allowed to stand while continuing heating at 100° C., to separate it into two layers. When the upper layer was collected and cooled down to room temperature, precipitation was observed. The precipitation was due to oligo (lactic acid), and the yield of the extraction was 35%. A determination of the molecular weight by gel permeation chromatography showed that the weight-average molecular weight was 250 (see Table 4 below).

Example 8

As in Example 1 above, 20 g of lactic acid fermentation liquor (pH 6) was obtained in which the concentration of ammonium lactate was 10 wt %. The cells of bacteria were removed from the lactic acid fermentation liquor as in Example 1. The pH of the lactic acid fermentation liquor was adjusted to 2.5 by addition of sulfuric acid. Subsequently, the lactic acid fermentation liquor was heated to 150° C., and kept under atmospheric pressure for 2 hours, under a reduced pressure of 100 torr (approximately 13300 Pa) for 2 hours, and then under a reduced pressure of 30 torr (approximately 4000 Pa) for 2 hours. Then, 50 ml of xylene was added thereto, and the mixture was heated to 100° C. with agitation. On hour later, the agitation was stopped and the mixture was allowed to stand while continuing heating at 100° C., to separate it into two layers. When the upper layer was collected and cooled down to room temperature, precipitation was observed. The precipitation was due to oligo (lactic acid), and the yield of the extraction was 60%. A determination of the molecular weight by gel permeation chromatography showed that the weight-average molecular weight was 637 (see Table 4 below).

Comparative Example 4

As in Example 1 above, 20 g of lactic acid fermentation liquor (pH 6) was obtained in which the concentration of ammonium lactate was 10 wt %. The cells of bacteria were removed from the lactic acid fermentation liquor as in Example 1. Here, the pH of the lactic acid fermentation liquor was not adjusted. Then, the lactic acid fermentation liquor was heated to 150° C., and kept under atmospheric pressure for 2 hours, under a reduced pressure of 100 torr (approximately 13300 Pa) for 2 hours, and then under a reduced pressure of 30 torr (approximately 4000 Pa) for 2 hours. Then, 50 ml of xylene was added thereto, and the mixture was heated to 100° C. with agitation. On hour later, the agitation was stopped and the mixture was allowed to stand while continuing heating at 100° C., to separate it into two layers. When the upper layer was collected and cooled down to room temperature, a small amount of precipitation was observed. The precipitation was due to oligo (lactic acid), and the yield of the extraction was 6%. A determination of the molecular weight by gel permeation chromatography showed that the weight-average molecular weight was 126. When the fermentation liquor was near neutral, the molecular weight was not significantly increased even with polymerization by heating under reduced pressure. Thus, the solubility was not significantly changed either, and the yield was low (see Table 4 below).

Example 9

As in Example 1 above, 20 g of lactic acid fermentation liquor (pH 6) was obtained in which the concentration of ammonium lactate was 10 wt %. The cells of bacteria were removed from the lactic acid fermentation liquor as in Example 1. The pH of the lactic acid fermentation liquor was adjusted to 2.5 by addition of sulfuric acid. Subsequently, the lactic acid fermentation liquor was heated to 150° C., and kept under atmospheric pressure for 2 hours, under a reduced pressure of 100 torr (approximately 13300 Pa) for 2 hours, and then under a reduced pressure of 30 torr (approximately 4000 Pa) for 2 hours. Then, 50 ml of water was added thereto, and the mixture was heated at 100° C. for 1 hour with agitation. On hour later, the agitation was stopped and the mixture was allowed to stand while continuing heating at 100° C., to separate it into two layers of a supernatant layer and a sediment layer. When the sediment layer was collected and cooled down to room temperature, precipitation was observed. The precipitation was due to oligo (lactic acid), and the yield was 80%. A determination of the molecular weight by gel permeation chromatography showed that the weight-average molecular weight was 637 (see Table 4 below).

Table 4 below collectively shows the results of heating the lactic acid fermentation liquor under reduced pressure.

TABLE 4

|  | pH | Condition for reaction | Product | Yield |
|---|---|---|---|---|
| Example 7 | 4.8 | Heating at 150° C. under reduced pressure followed by addition of xylene and heating to 100° C. | Oligo (Lactic acid) M.W. 250 | 35% |
| Example 8 | 2.5 | Heating at 150° C. under reduced pressure followed by addition of xylene and heating to 100° C. | Oligo (Lactic acid) M.W. 637 | 60% |
| Comparative Example 4 | 6 | Heating at 150° C. under reduced pressure followed by addition of xylene and heating to 100° C. | Oligo (Lactic acid) M.W. 126 | 6% |
| Example 9 | 2.5 | Heating at 150° C. under reduced pressure followed by addition of water and heating to 100° C. | Oligo (Lactic acid) M.W. 637 | 80% |

Example 10

An apparatus, the configuration of which is shown in FIG. 1, was used. In a lactic acid fermentation liquid medium that contained 3.5 wt % of standard medium M17 (manufactured by Difco Laboratories) for *streptococcus* supplemented with 20 wt % of glucose, lactic acid bacteria (lactobacillus bacteria) were subjected to lactic acid fermentation in suspension culture while the pH of the medium was adjusted with ammonia to near 6, and thus a lactic acid fermentation liquor (pH 6) was prepared, as an starting material, in which the concentration of ammonium lactate was 14 wt %. The cells of bacteria were removed in advance from the prepared lactic acid fermentation liquor by separation with a filter membrane.

The lactic acid fermentation liquor was sent to the pH adjusting vessel 5, where the pH of the lactic acid fermentation liquor was adjusted to 2.5 by addition of sulfuric acid, and subsequently was supplied via the liquid sending pump 6 to the reaction vessel 4. Furthermore, xylene was supplied from the solvent tank via the liquid sending pump 7 to the reaction vessel 4. The lactic acid fermentation liquor, the pH of which had been adjusted to 2.5, and xylene were heated at 100° C. for 2 hours with agitation. Then, the temperature was increased to 120° C. A vapor obtained from evaporation was condensed, water from which was removed, and then refluxed, and about 17 g of water was thus removed over approximately 5 hours (the total time for heating at 100° C. and heating at 120° C.), at the decanter 10. Subsequently, the mixture was heated to 139° C. Twenty hours later, the agitation was stopped and the mixture was allowed to stand, to separate it into two layers. When the upper layer was taken from the pipe 14 and cooled down to room temperature at the purifier 13, precipitation was observed. The precipitation was due to oligo (lactic acid), and the yield of the extraction was 63.6%. A determination of the molecular weight by gel permeation chromatography showed that the weight-average molecular weight was 1500. The degree of crystallization of the oligomer was as high as approximately 70%.

Example 11

As in Example 1 above, 20 g of lactic acid fermentation liquor (pH 6) was obtained in which the concentration of ammonium lactate was 10 wt %. The cells of bacteria were removed from the lactic acid fermentation liquor as in Example 1. The pH of the lactic acid fermentation liquor was adjusted to 2.0 by addition of sulfuric acid. Then, 200 ml of ethanol was added thereto, and the mixture was agitated at room temperature. Thirty minutes later, the agitation was stopped and the mixture was allowed to stand. Then, it was observed that the mixture was separated into precipitation at the lower layer and supernatant at the upper layer. The upper layer was taken, and ethanol was removed therefrom by evaporation, and thus, a viscous liquid was collected. The main component of the collected liquid was lactic acid, and the yield of the extraction was 95%.

Here, the precipitation was due to the medium components used for lactic acid fermentation and the salts used for neutralization or acidification of the lactic acid fermentation liquor A calculation based on the dry weight of the precipitation showed that 71.2 wt % of the components other than the collected lactic acid were separated and removed.

Example 12

In a lactic acid fermentation liquid medium that contained 1.3 wt % of synthetic medium for lactic acid supplemented with 14 wt % of glucose, lactic acid bacteria (lactococcus bacteria) were subjected to lactic acid fermentation in suspension culture while the pH of the medium was adjusted with ammonia to near 6, and thus 20 g of lactic acid fermentation liquor (pH 6) was obtained in which the concentration of ammonium lactate was 10 wt %. The synthetic medium contained ammonium sulfate, dipotassium hydrogen phosphate, potassium dihydrogen phosphate, sodium chloride, magnesium sulfate, calcium chloride, sodium carbonate, L-cysteine hydrochloride, and vitamins. The cells of bacteria were removed in advance from the lactic acid fermentation liquor by centrifugal separation. The pH of the lactic acid fermentation liquor was adjusted to 2.0 by addition of sulfuric acid. Then, 200 ml of ethanol was added thereto, and the mixture was agitated at room temperature. Thirty minutes later, the agitation was stopped and the mixture was allowed to stand. Then, it was observed that the mixture was separated into precipitation at the lower layer and supernatant at the upper layer. The upper layer was taken, and ethanol was removed therefrom by evaporation, and thus, a viscous liquid was collected. The main component of the collected liquid was lactic acid, and the yield of the extraction was 97%.

Here, the precipitation was due to the medium components used for lactic acid fermentation and the salts used for neutralization or acidification of the lactic acid fermentation liquor A calculation based on the dry weight of the precipitation showed that 76.5 wt % of the components other than the collected lactic acid were separated and removed.

Example 13

As in Example 12 above, 20 g of lactic acid fermentation liquor (pH 6) was obtained in which the concentration of ammonium lactate was 10 wt %. The cells of bacteria were removed from the lactic acid fermentation liquor as in Example 12. The pH of the lactic acid fermentation liquor was adjusted to 2.0 by addition of sulfuric acid. Subsequently, 200 ml of isopropyl alcohol was added thereto, and the mixture was agitated at room temperature. Thirty minutes later, the agitation was stopped and the mixture was allowed to stand. Then, it was observed that the mixture was separated into precipitation at the lower layer and supernatant at the upper layer. The upper layer was taken, and isopropyl alcohol was removed therefrom by evaporation, and thus, a viscous liquid was collected. The main component of the collected liquid was lactic acid, and the yield of the extraction was 98%.

Here, the precipitation was the medium components used for lactic acid fermentation and the salts used for neutralization or acidification of the lactic acid fermentation liquor. A calculation based on the dry weight of the precipitation showed that 82 wt % of the components other than the collected lactic acid were separated and removed.

Example 14

As in Example 12 above, 20 g of lactic acid fermentation liquor (pH 6) was obtained in which the concentration of ammonium lactate was 10 wt %. The cells of bacteria were removed from the lactic acid fermentation liquor as in Example 12. The pH of the lactic acid fermentation liquor was adjusted to 2.0 by addition of sulfuric acid. Subsequently, 100 ml of ethanol was added thereto, and the mixture was heated to 78° C. with agitation. Water was evaporated and removed together with ethanol to substantial dryness in approximately 2 hours. In the container, a viscous liquid and a slightly yellow-tinged white precipitate remained. Further, 100 ml of ethanol was added into the container, and the mixture was agitated at room temperature. Thirty minutes later, the agitation was stopped and the mixture was allowed to stand. Then, it was observed that the mixture was separated into precipitation at the lower layer and supernatant at the upper layer. The upper layer was taken, and ethanol was removed therefrom by evaporation, and thus, a viscous liquid was collected. The main component of the collected liquid was lactic acid, and the yield of the extraction was 95%.

Here, the precipitation was due to the medium components used for lactic acid fermentation and the salts used for neutralization or acidification of the lactic acid fermentation liquor. A calculation based on the dry weight of the precipitation showed that 90 wt % of the components other than the collected lactic acid were separated and removed.

Example 15

As in Example 12 above, 20 g of lactic acid fermentation liquor (pH 6) was obtained in which the concentration of ammonium lactate was 10 wt %. The cells of bacteria were removed from the lactic acid fermentation liquor as in Example 12. The pH of the lactic acid fermentation liquor was adjusted to 2.0 by addition of sulfuric acid. Subsequently, the lactic acid fermentation liquor was heated to 50° C., and kept under a reduced pressure of 10 torr (approximately 1330 Pa) for 2 hours, and then under a reduced pressure of 5 torr (approximately 670 Pa) for 2 hours to substantial dryness. Then, 100 ml of ethanol was added thereto, and the mixture was agitated. Thirty minutes later, the agitation was stopped and the mixture was allowed to stand, to separate it into supernatant and precipitation. The upper layer was taken, and ethanol was removed therefrom by evaporation, and thus, a viscous liquid was collected. The main component of the collected liquid was lactic acid, and the yield of the extraction was 90%.

Here, the precipitation was due to the medium components used for lactic acid fermentation and the salts used for neutralization or acidification of the lactic acid fermentation liquor. A calculation based on the dry weight of the precipitation showed that 94 wt % of the components other than the collected lactic acid were separated and removed.

Example 16

An apparatus, the configuration of which is shown in FIG. 1, was used. In a lactic acid fermentation liquid medium that contained 3.5 wt % of standard medium M17 (manufactured by Difco Laboratories) for *streptococcus* supplemented with 15 wt % of glucose, lactic acid bacteria (*lactobacillus* bacteria) were subjected to lactic acid fermentation in suspension culture while the pH of the medium was adjusted with ammonia to near 6, and thus a lactic acid fermentation liquor (pH 6) was prepared as a starting material in which the concentration of ammonium lactate was 10 wt %. The cells of bacteria were removed in advance from the prepared lactic acid fermentation liquor by separation with a filter membrane.

The lactic acid fermentation liquor was sent to the pH adjusting vessel 5, where the pH of the lactic acid fermentation liquor was adjusted to 2.0 by addition of sulfuric acid, and subsequently was supplied via the liquid sending pump 6 to the reaction vessel 4. Then, the lactic acid fermentation liquor, the pH of which had been adjusted to 2.0, was heated at 60° C. for 2 hours, while the pressure in the reaction vessel 4, the distillation column 8, and pipes connecting these constituent elements was reduced to 5 torr (approximately 670 Pa) by the vacuum pump (not shown) connected to the condenser 9. Thus, the lactic acid fermentation liquor in the reaction vessel 4 was dehydrated. Subsequently, ethanol was supplied from the solvent tank via the liquid sending pump 7 to the reaction vessel 4, and the mixture in the reaction vessel 4 was agitated. Thirty minutes later, the agitation was stopped and the mixture was allowed to stand, to separate it into two layers of supernatant and precipitation. The supernatant was taken from the pipe 14 and guided to the purifier 13, and the solvent was removed by evaporation from the supernatant by heating while the pressure was reduced by a vacuum pump (not shown) attached to the purifier 13, and thus, a viscous liquid was collected. The main component of the collected liquid was lactic acid, and the yield of the extraction was 98%. Here, the solvent removed by evaporation was ethanol, and may be cooled down and liquefied through the pipe 15, and used again as the extracting solvent.

According to the present invention, a lactic acid component (e.g., lactic acid or oligo (lactic acid)) can be obtained from a lactic acid fermentation liquor with a simple process. Accordingly, the present invention may be a fundamental technique to synthesize, at low cost, polymers such as polylactic acid and polyester polyol from the lactic acid component as a starting material.

The invention claimed is:

1. A method for producing oligo (lactic acid) from a lactic acid fermentation liquor, comprising the steps of:

providing a lactic acid fermentation liquor having a pH of greater than 4.8 of lactic acid fermentation by a microorganism, removing cells of the microorganism from the lactic acid fermentation liquor, and adjusting the pH of the lactic acid fermentation liquor to 4.8 or less;

adding at least one solvent selected from the group consisting of toluene, xylene, mesitylene, ethylbenzene, and mineral spirit, to the lactic acid fermentation liquor with a pH of 4.8 or less;

heating the solvent added lactic acid fermentation liquor with concurrent agitation for azeotropy and then to a temperature ranging from the azeotropic point of the solvent and water to 150° C., whereby the fermentation liquor is dehydrated and a lactic acid component in the fermentation liquor is condensed to produce oligo (lactic acid) with a weight-average molecular weight of not greater than 5000;

heating the solvent added fermentation liquor which contains the oligo (lactic acid) with agitation to a temperature ranging from 60° C. to 150° C. to dissolve the oligo (lactic acid) in the heated solvent for extraction;

stopping the agitation while keeping the heating to separate the solvent in which the oligo (lactic acid) is dissolved from the fermentation liquor; and cooling down the separated solvent to near room temperature to precipitate and collect the oligo (lactic acid).

2. A method for producing oligo (lactic acid) from a lactic acid fermentation liquor, comprising the steps of:

providing a lactic acid fermentation liquor having a pH of greater than 4.8 of lactic acid fermentation by a microorganism, removing cells of the microorganism from the lactic acid fermentation liquor, and adjusting the pH of the lactic acid fermentation liquor to 2.5 or less;

heating the lactic acid fermentation liquor with a pH of 2.5 or less to a temperature ranging from 100 to 150° C. under reduced pressure to produce oligo (lactic acid) with a weight-average molecular weight of at least 300 but not greater than 1000 by dehydration-condensation;

adding at least one solvent selected from the group consisting of toluene, xylene, mesitylene, ethylbenzene, and mineral spirit, to the fermentation liquor which contains the oligo (lactic acid);

heating the solvent added fermentation liquor which contains the oligo (lactic acid) with concurrent agitation to a temperature ranging from 60° C. to 150° C. to dissolve the oligo (lactic acid) in the heated solvent for extraction;

stopping the agitation while keeping the heating to separate the solvent in which the oligo (lactic acid) is dissolved from the fermentation liquor; and cooling down the separated solvent to near room temperature to precipitate and collect the oligo (lactic acid).

3. A method for producing oligo (lactic acid) from a lactic acid fermentation liquor, comprising the steps of:

providing a lactic acid fermentation liquor having a pH of greater than 4.8 of lactic acid fermentation by a microorganism, removing cells of the microorganism from the lactic acid fermentation liquor, and adjusting the pH of the lactic acid fermentation liquor to 2.5 or less;

heating the lactic acid fetinentation liquor with a pH of 2.5 or less to a temperature ranging from 100 to 150° C. under reduced pressure to produce oligo (lactic acid) with a weight-average molecular weight of at least 300 but not greater than 1000 by dehydration-condensation; and washing the fermentation liquor which contains the oligo (lactic acid) with water to separate and collect the oligo (lactic acid) which is insoluble in the water.

* * * * *

UNITED STATES PATENT AND TRADEMARK OFFICE
CERTIFICATE OF CORRECTION

PATENT NO.         : 8,859,245 B2  
APPLICATION NO.    : 12/294376  
DATED              : October 14, 2014  
INVENTOR(S)        : Hiroshi Uyama et al.

It is certified that error appears in the above-identified patent and that said Letters Patent is hereby corrected as shown below:

In the Claims

Column 30, Line 15, Claim 3, delete "fetinentation" and insert -- fermentation --

Signed and Sealed this
Tenth Day of February, 2015

Michelle K. Lee
*Deputy Director of the United States Patent and Trademark Office*